United States Patent [19]

Suganuma

[11] Patent Number: 5,750,743
[45] Date of Patent: May 12, 1998

[54] METHOD FOR PREPARING A SOLUTION OF AN ALKALI SALT OF ANTHRAHYDROQUINONE

[75] Inventor: Hiroyuki Suganuma, Kawasaki, Japan

[73] Assignee: Kawasaki Kasei Chemicals Ltd., Tokyo, Japan

[21] Appl. No.: 766,469

[22] Filed: Dec. 12, 1996

[30] Foreign Application Priority Data

Dec. 21, 1995 [JP] Japan .................................. 7-333818

[51] Int. Cl.[6] .................................................. C07C 37/86
[52] U.S. Cl. .......................................... 552/271; 552/208
[58] Field of Search ................................ 552/271, 208; 508/733, 762

[56] References Cited

PUBLICATIONS

Lion Corp., Chemical Abstracts, vol. 98, No. 200109c., 1983.
Paba et al, Chemical Abstracts, vol. 119, No. 228358j., 1993.
Miguel et al, Chemical Abstracts, vol. 116, No. 105792b., 1992.
Patent Abstracts of Japan, vol. 005, No. 164 (C–076), Oct. 21, 1981, JP–A–56 092234, Jul. 25, 1981.

*Primary Examiner*—James H. Reamer
*Attorney, Agent, or Firm*—Oblon, Spivak, McClelland, Maier & Neustadt, P.C.

[57] ABSTRACT

A method for preparing a solution of an alkali salt of anthrahydroquinone, which comprises reacting a solution of an alkali salt of 1,4-dihydro-9,10-dihydroxyanthracene with anthraquinone in the presence of an alkali.

7 Claims, No Drawings

METHOD FOR PREPARING A SOLUTION OF AN ALKALI SALT OF ANTHRAHYDROQUINONE

The present invention relates to a simple method for preparing a solution of an alkali salt of anthrahydroquinone (hereinafter, mere indication of an alkali salt of an anthrahydroquinone compound typically represents a dialkali salt such as a disodium salt) to be used as a cooking aid for pulp. Further, it relates to a simple method for preparing a solution of an alkali salt of anthrahydroquinone which is useful as a material for fine granular anthraquinone (9,10-anthraquinone will hereinafter be referred to simply as anthraquinone) to be used as an inhibitor of sulfides generation in a water system wherein sulfate-reducing bacteria and sulfate ions are present, such as sludge, industrial waste water, sanitary waste water of building sump pits, sewage, anaerobic treating system or oil field waste water, or which is useful as such an inhibitor by itself. Furthermore, it relates to a simple method for preparing a solution of an alkali salt of anthrahydroquinone of high purity, which can be used for preparation of a solid phase redox catalyst utilizing the reducing ability of anthrahydroquinone.

A solution of an alkali salt of 1,4-dihydro-9,10-dihydroxyanthracene (hereinafter referred to as DDA), for example, an aqueous solution of a disodium salt of DDA, is commonly used not only in Japan but worldwidely as a cooking aid for pulp against lignocellulose material of e.g. wood. It is known that such a solution is superior in penetrability into chips, since it can be added to the cooking system in the form of a solution, as compared with anthraquinone used for the same purpose but added in a solid form (such as a slurry having fine powder dispersed in an aqueous medium), and thus, it tends to have higher effects as a cooking aid.

It is reported that such an aqueous solution of a disodium salt of DDA added as a cooking aid, carries out a redox reaction in the cooking system and will eventually be converted to anthraquinone, and further the anthraquinone and anthrahydroquinone undergo a redox reaction, to provide cooking aid effects, whereby lignin is removed from the lignocellulose material.

Accordingly, if it becomes possible to readily produce a solution of an alkali salt of anthrahydroquinone, such a solution of an alkali salt of anthrahydroquinone can also be added in the form of a solution in the same manner as the above-mentioned aqueous solution of a disodium salt of DDA and can be used as a cooking aid for pulp which is excellent in penetrability into chips and which provides sufficient effects as compared with anthraquinone. For example, a comparison in effects in soda cooking has been reported (Appita, 32 (2), 117 (1978), T. J. Fullerton).

As conventional methods for preparing such a solution of an alkali salt of anthrahydroquinone, the following three methods may be mentioned as typical methods.

(1) A method for preparing a solution of an alkali salt of anthrahydroquinone by an isomerization reaction by heating and dissolving 1,4-dihydroanthraquinone (hereinafter referred to as DHAQ) in an alkali solution.

(2) A method for preparing a solution of an alkali salt of anthrahydroquinone by reducing anthraquinone by means of hydrosulfite or saccharides, or other compounds having reducing ability i.e. so-called reducing agents, in an alkali solution.

(3) A method for preparing a solution of an alkali salt of anthrahydroquinone by catalytically hydrogenating anthraquinone in an alkali solution in the presence of a hydrogenation catalyst such as palladium.

However, these methods have problems respectively. For example, in the method (1), DHAQ as the starting material is readily oxidized to anthraquinone, whereby it is very difficult to selectively produce DHAQ in high purity, and at present, it is hardly available as a commercial product. Thus, this method is not practical. In the method (2), it is necessary to use in excess of the theoretical amount of the compound which serves as a reducing agent in the alkali solution, in order to completely reduce the anthraquinone to anthrahydroquinone, and consequently, the excessive reducing agent, a by-product from this reducing agent (for example, a sulfite from hydrosulfite) and a decomposition product of the reducing agent itself tend to remain in the resulting solution of an alkali salt of anthrahydroquinone, whereby it will be difficult to produce a solution of an alkali salt of anthrahydroquinone in high purity. In the method (3), it is possible to obtain a solution of an alkali salt of anthrahydroquinone having a relatively high purity free from by-products or decomposition products, as is different from the method (2). However, an expensive catalyst for reduction is required, and a special equipment is required to handle high pressure hydrogen gas. Thus, this method has a drawback that the production cost is high.

It is an object of the present invention to develop a simple and low cost process for producing a solution of an alkali salt of anthrahydroquinone free from a reducing agent, its by-product or decomposition product.

The present inventor has conducted an extensive study to accomplish the above object and as a result has found a surprising fact that when a solution of an alkali salt of DDA and an equimolar amount of anthraquinone are heated in the presence of an alkali in an amount of at least 2 mol per mol of the anthraquinone, the alkali salt of DDA acts as a reducing agent against anthraquinone to form an alkali salt of anthrahydroquinone, and at the same time, the alkali salt of DDA will not only be oxidized to DHAQ but also readily isomerized to an alkali salt of anthrahydroquinone.

Namely, what is consequently obtainable by the reaction of the present invention, is an alkali salt of anthrahydroquinone, into which both the alkali salt of DDA and the anthraquinone have changed. For example, in a case where a sodium salt is used as an alkali salt of DDA and sodium hydroxide is used as the alkali, this reaction may be represented by the following reaction scheme 1.

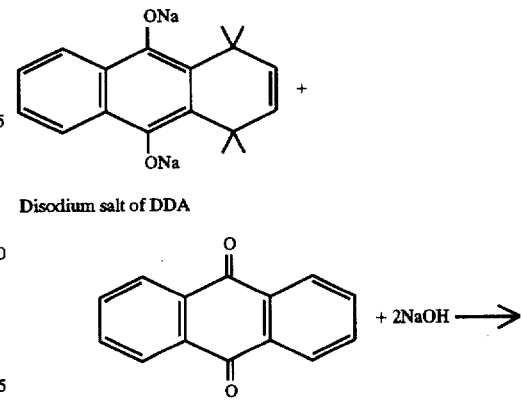

-continued
Reaction Scheme 1

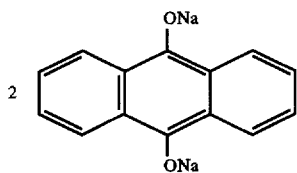

The present invention provides (1) a method for preparing a solution of an alkali salt of anthrahydroquinone, which comprises reacting a solution of an alkali salt of DDA with anthraquinone in the presence of an alkali, (2) the method (1) wherein the solution of an alkali salt of DDA is an aqueous solution of a disodium salt of DDA, (3) the method (1) wherein the alkali is a strongly alkaline compound, (4) the method (3) wherein the strongly alkaline compound is a hydroxide of an alkali metal, (5) the method (1) wherein the alkali is in an amount of at least 2 mol per mol of the anthraquinone, and (6) the method (1) wherein the reaction is carried out at a temperature of from 5° to 200° C.

Now, the present invention will be described in detail with reference to the preferred embodiments.

When contacted with a solution of an alkaline compound, especially with a strongly alkaline compound, DDA will dissolve mainly in the form of its salt, although the solubility varies. As such a strongly alkaline compound, an alkali metal hydroxide such as sodium hydroxide or potassium hydroxide, or a quaternary ammonium hydroxide such as tetramethylammonium hydroxide, may, for example, be mentioned. As the corresponding alkali salt of DDA formed by the neutralization reaction, the respectively corresponding dialkali metal salt such as a disodium salt or a dipotassium salt, or a diquaternary ammonium salt, may, for example, be mentioned.

In the present invention, the above solution of an alkali salt of DDA may readily be obtained in the form of an aqueous solution, for example, by the following method. Namely, 1,4,4a,9a-tetrahydroanthraquinone (hereinafter referred to as THAQ) obtained by a Diels Alder reaction of 1,4-naphthoquinone with 1,3-butadiene, is contacted with an aqueous alkaline solution containing at least the equivalent (i.e. at least 2 mols per mol of THAQ) of an alkaline compound such as sodium hydroxide or potassium hydroxide, whereby THAQ will be isomerized to DDA, and an aqueous solution of an alkali salt of DDA will be obtained. For the industrial purpose, this aqueous solution is obtained usually in the form of a from 20 to 23 wt % aqueous solution which is close to the solubility of the water-soluble salt of DDA at room temperature (hereinafter the concentration of the water-soluble salt of DDA will be represented in all cases by a concentration calculated as anthraquinone), taking into consideration the efficiency of the apparatus such as production facilities.

Therefore, the aqueous solution having such a concentration may be used as it is, as the aqueous solution of an alkali salt of DDA to be used in the present invention, so long as it is thereby possible to obtain a solution of an alkali salt of anthrahydroquinone at a concentration suitable for the conditions of the present invention. Otherwise, a solution having a concentration lower than such a concentration, may be used.

In the present invention, it is usual to employ such an aqueous solution as described above, as the solution of an alkali salt of DDA. However, so long as DDA and an alkali salt of anthrahydroquinone are dissolved, other medium such as an alcohol may be present.

Further, instead of using a solution of an alkali salt of DDA as the starting material, the present invention may be carried out also by a method wherein THAQ and an equimolar amount of anthraquinone are added to and reacted with a solution containing an alkali in an amount of at least 4 mol per mol of THAQ.

Namely, as mentioned above, THAQ is isomerized to DDA and dissolves in the form of an alkali salt of DDA, followed by the same reaction as the above described present invention to obtain a solution of an alkali salt of anthrahydroquinone. For example, in a case where sodium hydroxide is used as the alkali, the reaction may be represented by the following reaction scheme 2.

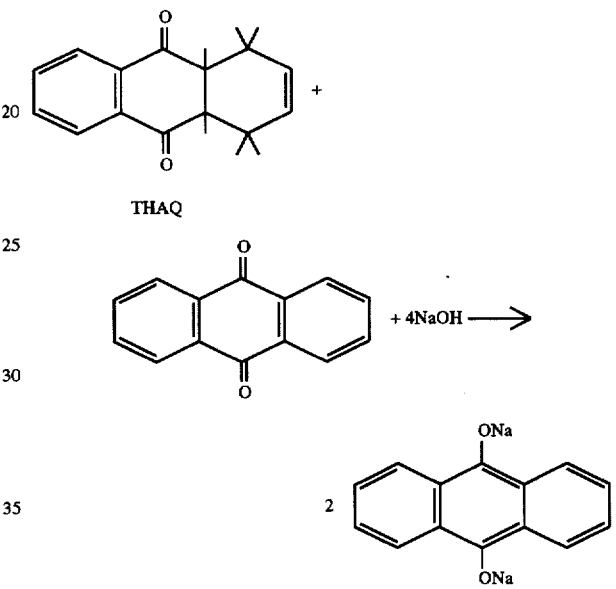

Theoretically, anthraquinone may be used in an equimolar amount to an alkali salt of DDA. However, it may be used in more or less than the equimolar amount, as the case requires. If it is used less than the equimolar amount, an unreacted alkali salt of DDA will mainly remain, but this method may be employed, if such a residue is allowable depending upon the particular purpose of use.

On the other hand, in a case where an alkali salt of DDA and at least an equimolar amount of anthraquinone are used, unreacted and excess anthraquinone will remain as a slurry in the resulting solution of an alkali salt of anthrahydroquinone. Such remaining anthraquinone may be removed by decantation or filtration, as the case requires, to obtain a solution of an alkali salt of anthrahydroquinone.

Specifically, anthraquinone is used usually in an equimolar amount to the alkali salt of DDA. However, it may be used within a range of from 0.7 to 1.1 mol per mol of the alkali salt, taking into consideration the reaction rate and post treatment for e.g. removal of unreacted anthraquinone.

In the present invention, it is possible to employ, as the anthraquinone, powdery anthraquinone which is available industrially. Usually, the one having an average particle size of about 30 μm, is readily available. However, if necessary, such powdery anthraquinone may further be grinded for use. By reducing the particle size, it is also possible to increase the reaction rate. An aqueous medium may be present during the grinding, so that anthraquinone may be used in the form of a slurry.

Further, an alkali solution slurry of anthraquinone obtainable by oxidizing the solution of a dialkali salt of DDA with air, may be directly mixed with a solution of a dialkali salt of DDA and reacted under heating.

As the alkali to be used for the reaction, a hydroxide of an alkali metal or a strongly alkaline compound such as a quaternary ammonium, is preferred. From the viewpoint of the solubility and the reactivity, sodium hydroxide or potassium hydroxide may be mentioned as the alkali metal hydroxide. From the viewpoint of the cost and handling efficiency, sodium hydroxide is particularly preferred.

The amount of the alkali to be used for the reaction is usually at least 2 mol, usually from 2.02 to 2.10 mol, per mol of the anthraquinone to be added. The presence of an excess amount of the alkali accelerates the reaction. However, if the excess amount of the alkali is large, such an excess amount adds to the cost. On the other hand, if the amount of the alkali to be added is insufficient, not only unreacted anthraquinone will remain, but also conversion of the alkali salt of DDA (such as a disodium salt of DDA) to anthrone is occurred.

When an alkali of a type different from the alkali constituting the alkali salt of DDA, is used as the alkali for the reaction, the resulting alkali salt of anthrahydroquinone will be a mixture of such alkali salts. Such a combination of alkalis is acceptable so long as there is no problem in its use.

The reaction is carried out usually at a temperature of at least 50° C., preferably at least 60° C., more preferably from 90 to 200° C. If the reaction temperature is lower than 50° C., the reaction rate will be low. The higher the reaction temperature, the higher the reaction rate. However, it is usually sufficient to carry out the reaction under atmospheric pressure for from 2 to 4 hours at 90° C., or from 1 to 2 hours at 100° C. However, the reaction may be carried out under pressure, as the case requires.

The concentration of the resulting alkali salt of anthrahydroquinone is preferably at a level of at most 20 wt % as calculated as anthraquinone, in order to avoid precipitation of the dialkali salt of anthrahydroquinone. However, in a case where the product can be handled under heating, it is possible to prepare it in the form of a solution of an alkali salt of anthrahydroquinone having a higher concentration.

As the pulp cooking aid, it can be used in the same manner as a known cooking aid. For example, the aqueous solution of an alkali salt of anthrahydroquinone obtained by the present invention, may be advantageously used by a method of supplying it in a liquid state by a pipeline, in an alkali cooking method such as a soda method (effective alkali: 8 to 20 wt %), a craft method (effective alkali: 14 to 20 wt %, sulfidity: 10 to 30 wt %), a polysulfide cooking method or a sulfide cooking method.

The solution of an alkali salt of anthrahydroquinone obtained by the present invention, can be used as starting material for an inhibitor of sulfide generation, or as such an inhibitor. The "sulfate-reducing bacteria" to be thereby inhibited, may be any bacteria irrespective of their genus or species, so long as they are capable of reducing a sulfate as the term indicates. For example, they may be bacteria such as *Desulfovibrio desulfuricans, Desulfovibrio baarsii* or *Desulfovibrio sapovorans*, as disclosed in "Useful Water and Waste Water", vol. 31, No. 4, p. 294–305 (1989). To use the solution of an alkali salt of anthrahydroquinone obtained by the present invention as such an inhibitor of a sulfide generation, it may be added as it is to a water system wherein the sulfate-reducing bacteria and sulfate ions are present, and hydrogen sulfide is formed. As such a water system, sludge, industrial waste water, sanitary waste water of building sump pits, sewage, anaerobic treating system or oil field waste water may, for example, be mentioned. The industrial waste water may, for example, be waste water containing large amounts of organic substances, organic sulfonates, sulfites and sulfates discharged from a pulp plant, a leather plant or a petroleum plant. The sewage may, for example, be sewage in the pipeline installation, in a pumping station or in the sewage treatment plant. The oil field waste water may, for example, be effluent water at a petroleum oil field.

When the solution of an alkali salt of anthrahydroquinone of the present invention is used as an inhibitor of a sulfide generation, it may usually be added to the water-system in an amount of from 0.05 to 100 ppm, usually from 0.1 to 50 ppm, preferably from 1 to 20 ppm, as anthrahydroquinone, although the amount may vary depending on various conditions including the energy source such as an organic acid, the amount of sulfate ions and the temperature in the water system.

Now, the present invention will be described in further detail with reference to Examples. However, it should be understood that the present invention is by no means restricted to such specific Examples.

EXAMPLE 1

In a nitrogen atmosphere, 26.3 g (0.658 mol) of sodium hydroxide was dissolved in 190 ml of water, and 28.5 g (0.134 mol) of THAQ was added thereto and dissolved at 60° C., to obtain a solution of a sodium salt of DDA. Further, 27.2 g (0.131 mol) of powdery anthraquinone (average particle size: 30 μm) was added thereto, and the mixture was heated to 95° C. and reacted for 2.5 hours.

As a result, the majority of anthraquinone was reacted and dissolved. After completion of the reaction, the reaction mixture was cooled to room temperature, and an unreacted residue was filtered off, to obtain 0.3 g (0.0014 mol) of anthraquinone as the filtration residue. Further, the concentration of the disodium salt of anthrahydroquinone contained in the filtrate, was examined by a method wherein it was oxidized with hydrogen peroxide to anthraquinone, whereupon the weight of the anthraquinone was measured, whereby the concentration was 19.9 wt %. The conversion of anthraquinone was 98.9%, as calculated from the anthraquinone as the filtration residue.

Further, the solution of the disodium salt of anthrahydroquinone thus obtained was added to acetic anhydride having oxygen removed in a nitrogen atmosphere, for acetylation, whereupon the product was isolated and identified by NMR, infrared absorption spectrum, mass spectrum and high performance liquid chromatography, whereby 9,10-diacetoxyanthracene formed from the disodium salt of anthrahydroquinone was at least 96 wt %, and the content of 1,4-dihydro-9,10-diacetoxyanthracene as an acetylated product of unreacted DDA, was 3 wt %.

EXAMPLE 2

In a nitrogen atmosphere, 8.0 g (0.20 mol) of sodium hydroxide was dissolved in 120 ml of an aqueous solution containing a disodium salt of DDA in an amount of 10.3 wt% as calculated as anthraquinone (specific gravity: 1.082, containing 0.0643 mol of DDA). Then, 10.0 g (0.0481 mol) of the same anthraquinone as used in Example 1 was added thereto, and the mixture was heated to 95° C. and reacted for 2 hours to dissolve the anthraquinone mostly.

Then, the post treatment and analyses were carried out in the same manner as in Example 1, whereby anthraquinone as the filtration residue was not more than 0.1 g, the concentration of the disodium salt of anthrahydroquinone in the filtrate was 16.2 wt % as anthraquinone, and the conversion of anthraquinone was at least 99%.

EXAMPLE 3

176.6 g of an aqueous solution containing 21 wt % of a disodium salt of DDA (containing 0.178 mol of DDA) was added to 162.7 g of an alkali aqueous solution slurry of anthraquinone (slurry concentration: 20.4 wt %, containing 0.160 mol of anthraquinone and 0.355 mol of sodium hydroxide) obtained by sufficiently oxidizing with air at 95° C. an aqueous solution containing a disodium salt of DDA in an amount of 21 wt % as calculated as anthraquinone, in a nitrogen atmosphere, and the mixture was reacted at 98° C. for 2 hours.

Then, the post treatment and analyses were carried out in the same manner as in Example 1, whereby anthraquinone as the filtration residue was 1.2 g, the concentration of the disodium salt of anthrahydroquinone in the filtrate was 20.6 wt % as anthraquinone, and the conversion of anthraquinone was 96.4%.

EXAMPLE 4

23.5 g of THAQ having a purity of 88% (containing 12% of DHAQ, THAQ: 0.0975 mol) and 20.0 g (0.0962 mol) of the same anthraquinone as used in Example 1 were added to an alkali solution having 21 g (0.525 mol) of sodium hydroxide dissolved in 180 ml of water, and the mixture was reacted at 95° C. for 2.5 hours to dissolve the anthraquinone mostly.

Then, the post treatment and analyses were carried out in the same manner as in Example 1, whereby anthraquinone as the filtration residue was 0.3 g, the concentration of the disodium salt of anthrahydroquinone in the filtrate was 17.1 wt % as anthraquinone, and the conversion of anthraquinone was 98.5%.

DHAQ contained in THAQ is all isomerized to anthrahydroquinone by heating in alkali, so that it is finally present in the form of a dialkali salt of anthrahydroquinone.

According to the present invention, it is possible to easily and inexpensively prepare a solution of an alkali salt of anthrahydroquinone by reacting anthraquinone and an alkali salt of DDA, which are produced industrially in a large quantity at a relatively low cost and which are readily available. It is thereby possible to overcome the conventional difficulty with respect to the cost, so that it becomes possible to use such a solution as a cooking aid for pulp or for other industrial applications.

I claim:

1. A method for preparing a solution of an alkali salt of anthrahydroquinone, which comprises reacting a solution of a dialkali salt of 1,4-dihydro-9,10-dihydroxyanthracene with anthraquinone in the presence of at least 2 mols per mol of said anthraquinone of an alkali.

2. The method according to claim 1, wherein the solution of said alkali salt of 1,4-dihydro-9,10-dihydroxyanthracene is an aqueous solution of a disodium salt of 1,4-dihydro-9,10-dihydroxyanthracene.

3. The method according to claim 1, wherein the alkali is a strongly alkaline compound.

4. The method according to claim 3, wherein the strongly alkaline compound is a hydroxide of an alkali metal.

5. The method according to claim 1, wherein the reaction is carried out at a temperature of from 50° to 200° C.

6. A method for preparing a solution of an alkali salt of anthrahydroquinone, which comprises reacting 1,4,4a,9a-tetrahydroanthraquinone with anthraquinone in a solution containing at least 4 mols per mol of said 1,4,4a,9a-tetrahydroanthraquinone of an alkali.

7. The method according to claim 1, wherein said dialkali salt is reacted with an about equimolar amount of anthraquinone.

* * * * *